United States Patent
Thevenieau et al.

(10) Patent No.: US 10,278,933 B2
(45) Date of Patent: May 7, 2019

(54) TRIACYLGLYCEROL-BASED LIPID COMPOSITION

(71) Applicants: AVRIL, Paris (FR); UNIVERSITE PARIS-SUD, Orsay (FR)

(72) Inventors: France Thevenieau, Chartres (FR); Sophie Sambou, Fosses (FR); Marie-Joëlle Virolle, Bures sur Yvette (FR); Thierry Dulermo, Saint Germain en Laye (FR)

(73) Assignees: AVRIL, Paris (FR); UNIVERSITE PARIS-SUD, Orsay (FR)

( * ) Notice: Subject to any disclaimer, the term of this patent is extended or adjusted under 35 U.S.C. 154(b) by 0 days.

(21) Appl. No.: 14/898,926

(22) PCT Filed: Jun. 20, 2014

(86) PCT No.: PCT/IB2014/062488
§ 371 (c)(1),
(2) Date: Dec. 16, 2015

(87) PCT Pub. No.: WO2014/203219
PCT Pub. Date: Dec. 24, 2014

(65) Prior Publication Data
US 2016/0143872 A1 May 26, 2016

(30) Foreign Application Priority Data
Jun. 21, 2013 (FR) ..................... 13 55963

(51) Int. Cl.
| *A61K 31/201* | (2006.01) |
| *A23D 9/00* | (2006.01) |
| *C11C 3/00* | (2006.01) |
| *A61K 8/04* | (2006.01) |
| *A61K 8/36* | (2006.01) |
| *A61K 31/20* | (2006.01) |
| *A61Q 5/06* | (2006.01) |
| *C10M 105/24* | (2006.01) |

(52) U.S. Cl.
CPC .............. *A61K 31/201* (2013.01); *A23D 9/00* (2013.01); *A61K 8/046* (2013.01); *A61K 8/361* (2013.01); *A61K 31/20* (2013.01); *A61Q 5/06* (2013.01); *C10M 105/24* (2013.01); *C11C 3/00* (2013.01); *A61K 2800/5922* (2013.01)

(58) Field of Classification Search
CPC ........ A23D 9/00; A61K 31/20; A61K 31/201; A61K 8/046; A61K 8/361; A61K 2800/5922; A61Q 5/06; C10M 105/24; C10M 105/42; C11C 3/00; C11C 3/02
See application file for complete search history.

(56) References Cited

U.S. PATENT DOCUMENTS

| 5,104,678 A * | 4/1992 | Yang ........................ A23D 9/00 426/417 |
| 2005/0143463 A1 | 6/2005 | Krishnan |

FOREIGN PATENT DOCUMENTS

EP 2390341 11/2011

OTHER PUBLICATIONS

Pazos et. al., Comparative Biochemistry and Physiology Part B, 2003, Elsevier, vol. 134, pp. 367-380.*
Cuvelier, C., et al., "Acides gras: nomenclature et sources alimentaires," Ann. Med. Vet., 2004, pp. 133-140, vol. 148.
Folch, J., et al., "A simple method for the isolation and purification of total lipides from animal tissues," 1957, pp. 497-509, vol. 226, The Journal of Biological Chemistry.
International Search Report for International Application No. PCT/IB2014/062488 dated Oct. 22, 2014.
Kimoto-Nira, H., et al., "Bile resistance in Lactococcus lactis strains varies with cellular fatty acid composition: Analysis by using different growth media," Jan. 22, 2009, pp. 183-188, vol. 131, No. 2-3, International Journal of Food Microbiology, Elsevier, BV, NL.
Written Opinion of the International Searching Authority for International Application No. PCT/IB2014/062488 dated Oct. 22, 2014.

* cited by examiner

*Primary Examiner* — Sarah Pihonak
(74) *Attorney, Agent, or Firm* — Dinsmore & Shohl LLP (57) ABSTRACT

The invention relates to a lipid composition comprising fatty acids mainly in the form of triacylglycerols, in which composition at least 50% of the fatty acids are 14-methyl pentadecanoic acids, and at least 8% of the fatty acids are 12-methyl tetradecanoic acids, the percentages being expressed by weight with respect to the total fatty acids of the composition.

15 Claims, 3 Drawing Sheets

TRIACYLGLYCEROL-BASED LIPID COMPOSITION

CROSS REFERENCE TO RELATED APPLICATIONS

This application is the National Phase filing of International Appln. No. PCT/IB2014/062488, filed 20 Jun. 2014, and claims priority benefit of French Appln. No. 1355963, filed 21 Jun. 2013, the entireties of which applications are incorporated herein by reference for all purposes.

FIELD OF THE INVENTION

The present invention relates to lipid compositions based on triacylglycerols (TAGs) and to the various applications thereof.

BACKGROUND OF THE INVENTION

Lubricants are fatty substances which make it possible to reduce friction between two surfaces. They are mainly composed of a basic oil and of additives which give them particular properties. The oils used are generally of mineral, vegetable, animal or synthetic origin, and can be recycled.

Following the depletion of petroleum resources and the appearance of numerous studies demonstrating the negative impact on the environment of the compounds resulting from the petrochemical industry, oils of vegetable or animal origin tend to replace oils of petrochemical origin for applications in many fields, in particular in the lubricant field.

The use of biolubricants has emerged over the past few years (oil of vegetable or animal origin) and, although it is advantageous from an ecological point of view, it still remains marginal (less than 5% of the lubricant market) owing to the very high production costs compared with lubricants of petrochemical origin and the difficulties in supplying vegetable oils requiring large-scale crops (oleaginous crops) often intended for human or animal food.

Nevertheless, the use of these biolubricants proves to be very advantageous, in particular in applications where the recovery of the lubricants is virtually impossible or subject to accidental losses (in soils and water), since their environmental impact is limited and they make it possible to minimize health risks.

Consequently, in a perspective of developing products that are more environmentally friendly, vegetable and animal oils are used in various applications.

The document "Acides gras: nomenclature et sources alimentaires" ["Fatty acids: nomenclature and food sources"], by Cuvier C Cabaraux J.-F., Dufrasne I., Hornick J.-L., Istasse L. Manuscrit *Ann. Méd. Vét.*, 2004, 148, 133-140, describes the fatty acid content of the lipid compositions of various products of animal or vegetable origin: rapeseed oil, corn oil, sunflower oil, olive oil, linseed oil, etc.

Lipid compositions based on triacylglycerols are described in patent application NESTLE OIL OYJ EP 2 390 341, resulting from a process of lipid synthesis by a microorganism. The study relates to the accumulation of TAGs in the cytoplasm by the microorganism.

SUMMARY OF THE INVENTION

There is a need for a biodegradable, nontoxic and/or biobased alternative lipid source.

To this effect, the invention relates to a lipid composition comprising fatty acids mainly in the form of triacylglycerols, in which:
  at least 50% of the fatty acids are 14-methylpentadecanoic acids, in particular at least 55% of the fatty acids are 14-methylpentadecanoic acids, and
  at least 8% of the fatty acids are 12-methyltetradecanoic acids,
  the percentages being expressed by weight of the total fatty acids of the composition.

DETAILED DESCRIPTION OF THE INVENTION

The term "lipid composition" is intended to mean a composition comprising at least 50% of lipids, said percentage being expressed by total weight of the composition. The composition advantageously comprises at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95$, 96%, 97%, 98% or 99% of lipids, said percentages being expressed by total weight of the composition. The composition may comprise any other constituent in accordance with the abovementioned lipid proportions.

This lipid composition comprises fatty acids which are mainly in the form of TAGs.

The expression "fatty acids mainly in the form of triacylglycerols" is intended to mean that at least half (at least 50% by total weight of the total fatty acids of the composition) of the fatty acids present in the composition are esterified on a triacylglycerol molecule. The composition advantageously comprises at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the fatty acids in the form of triacylglycerols, these percentages being expressed by total weight of the fatty acids of the composition.

The composition according to the invention therefore constitutes an advantageous and alternative source of TAGs, which are easily extractable and present in large amounts. Since TAGs are the main constituents of oils, they are chemical compounds with a strong industrial potential. They are in particular known to have a natural lubricating capacity and good adhesiveness to metal surfaces.

Furthermore, as will be specified hereinafter, the composition according to the invention comprises fatty acids with a short aliphatic chain which can comprise particular units, for instance the presence of a methyl group on the penultimate or antepenultimate carbon atom of the chain, or else of a hydroxyl group.

Advantageously, the composition according to the invention comprises a majority of saturated fatty acids. It also comprises unsaturated fatty acids in a lesser amount, said unsaturated fatty acids having a low number of unsaturations (preferably less than three). These various characteristics confer improved properties on the composition: better behavior of the oil at low temperature, good resistance to thermal oxidation and/or better fluidity.

Moreover, a composition according to the invention can be obtained by chemical synthesis and/or by biological synthesis by means of a process using a microorganism.

Since the fatty acids of the composition according to the invention are commercially available, those skilled in the art can easily carry out an esterification reaction in the presence of glycerol in order to obtain a mixture of monoacylglycerols, diacylglycerols and triacylglycerols. The nature of the fatty acids and the proportions according to the invention will be predetermined, and easily predeterminable by those skilled in the art.

The composition can also be synthesized by a microorganism, in a nutritional medium comprising a carbon source, in particular glycerol, glucose or any other less refined carbon source originating, for example, from agro-industry waste such as organic industrial waste or residues, agricultural organic waste, municipal waste or microbial waste, or mixtures thereof.

Increased accumulation of TAGs in the cytoplasm of the microorganism can be promoted by using glycerol as main carbon source, by a step of phosphate or nitrogen hypercompensation, or by a mixture (glycerol and hypercompensation).

Culturing in a nutrient-rich medium and then in a nutrient-poor medium is known from the prior art as "hypercompensation".

In the context of organic or inorganic phosphate hypercompensation, 2.5 mM to 50 mM of inorganic phosphate, preferentially from 3 mM to 40 mM, more particularly from 4 mM to 30 mM, even more particularly from 5 mM to 20 mM, in particular from 5 mM to 10 mM of inorganic phosphate is advantageously added to the preculture medium.

Advantageously, glycerol, which is readily accessible from the oleaginous path, can be used as crude or refined carbon source.

14-Methylpentadecanoic acid is also referred to by its usual name "isohexadecanoic fatty acid" or by its physiological nomenclature "iso 016:0".

12-Methyltetrodecanoic acid the usual name of which is "anteiso-heptadecanoic fatty acid", is also known by its physiological nomenclature "anteiso 015:0".

Preferably, the composition comprises at least 55% of triacylglycerols, the percentage being expressed by total weight of the composition. More advantageously, the composition comprises at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of triacylglycerols, the percentages being expressed by total weight of the lipid composition.

Advantageously, the composition comprises mainly compounds derived from biomass (biosynthesized), more advantageously all the compounds of the composition are derived from biomass.

Advantageously, the lipid composition of the invention comprises at least 55% of 14-methylpentadecanoic acid, by weight of the total fatty acids of the composition. Preferably, the composition comprises at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% of 14-methylpentadecanoic acid, the percentage being expressed by weight of the total fatty acids of the composition.

According to one advantageous embodiment, the composition according to the invention defined above also comprises from 6.5% to 20% of 12-methyltridecanoic fatty acid, the percentages being expressed by weight of the total fatty acids of the composition.

12-Methyltridecanoic acid is also known by its usual name "isotetradecanoic fatty acid" or by its physiological nomenclature "iso 014:0".

Preferably, the composition according to the invention comprises 7%, 8%, 9%, 10%, 11%, 12%, 13%, 14%, 15%, 16%, 17%, 18%, 19% or 20% of 12-methyltridecanoic fatty acid, the percentages being expressed by total weight of the composition.

Likewise advantageously, the composition according to the invention comprises at least 50% of 14-methylpentadecanoic acid, at least 8% of 12-methyltetrodecanoic acids and from 6.5% to 20% of 12-methyltridecanoic fatty acid, the percentages being expressed by weight of the total fatty acids of the composition.

According to one advantageous embodiment, the composition according to the invention defined above also comprises from 6.5% to 20% of 14-methylhexadecanoic fatty acid, the percentages being expressed by weight of the total fatty acids of the composition.

14-Methylhexadecanoic acid is also known by its usual name "anteiso-heptadecanoic fatty acid" or by its physiological nomenclature "anteiso 017:0".

Preferably, the composition according to the invention comprises 7%, 8%, 9%, 10%, 11%, 12%, 13%, 14%, 15%, 16%, 17%, 18%, 19% or 20% of 14-methylhexadecanoic fatty acid, the percentages being expressed by total weight of the composition.

Likewise advantageously, the composition comprises at least 50% of 14-methylpentadecanoic acid, at least 8% of 12-methyltetrodecanoic acids, from 6.5% to 20% of 12-methyltridecanoic fatty acid and/or from 6.5% to 20% of 14-methylhexadecanoic fatty acid, the percentages being expressed by weight of the total fatty acids of the composition.

According to one advantageous embodiment, the composition according to the invention defined above comprises at least 8% of 12-methyltetrodecanoic fatty acid, the percentage being expressed by weight of the total fatty acids of the composition.

According to one advantageous embodiment, the composition according to the invention defined above comprises fatty acids having a carbon-based chain of from 8 to 22 carbon atoms.

Preferably, the carbon-based chain has 9, 10, 11, 12, 13, 14, 15, 16, 17, 18, 19 or 20 carbon atoms, more preferably from 14 to 17 carbon atoms.

The fatty acids, which are linear or branched, may be hydroxylated and/or methylated, i.e. the carbon-based chains are substituted with at least one hydroxyl and/or methyl group.

The position of the methyl group advantageously varies between the penultimate carbon atom starting from the terminal methyl group (iso) and the antepenultimate (anteiso).

Advantageously, the composition according to the invention comprises mainly saturated fatty acids. Preferably, the composition comprises at least 60% of saturated fatty acids, the percentage being expressed by total weight of the fatty acids of the composition.

Advantageously, at least 50% of the unsaturated fatty acids present in the composition according to the invention are monounsaturated, the percentage being expressed by total weight of the unsaturated fatty acids. Preferably, at least 70% of the unsaturated fatty acids are monounsaturated, more preferably 90% of the unsaturated fatty acids are monounsaturated.

According to one even more advantageous embodiment, the composition according to the invention comprises at least the fatty acids chosen from 12-methyltridecanoic acid (iso C14:0/iso-tetradecanoic acid), tetradecenoic acid (C14:1), 12-methyltetrodecanoic acid (anteiso C15:0/anteiso-pentadecanoic acid), pentadecanoic acid (C15:0), 14-methylpentadecanoic acid (iso C16:0/iso-hexadecanoic acid), 14-methylpentadecenoic acid (iso C16:1/iso-hexadecenoic acid), hexadecanoic acid (C16:0), hexadecenoic acid (C16:1), 15-methylhexadecanoic acid (iso C17:0/iso-heptadecanoic acid), heptadecanoic acid (C17:0), heptadecenoic acid (C17:1) and/or 14-methylhexadecanoic acid (anteiso C17:0/anteiso-heptadecanoic acid).

Preferably, all the fatty acids of the composition are chosen from those mentioned above.

According to one even more advantageous embodiment, the total fatty acids of the composition are present in the proportions as defined hereinafter:
from 6.7% to 7.7% of iso C14:0,
from 3.1% to 4% of C14:1,
from 9.8% to 11% of anteiso C15:0,
from 0.1% to 0.7% of C15:0,
from 61.5% to 62.5% of iso C16:0,
from 0.5% to 1.5% of iso C16:1,
from 3.1% to 4% of C16:0,
from 0.1% to 7.7% of C16:1,
from 0.5% to 1.5% of C17:0,
from 0.5% to 1.5% of C17:1,
from 1.1% to 2.1% of iso C17:0, and
from 6.7% to 7.7% of anteiso C17:0,
the percentages being expressed by weight of the total fatty acids of the composition.

The composition according to the invention may also comprise any other type of lipids and/or impurities, the lipids being for example free fatty acids, oligomers, sterols, fatty acid esters, sterol esters, monoacylglycerols and/or diacylglycerols.

The composition may comprise up to 49% of impurities, the percentage being expressed by total weight of the composition. The impurities may be cell debris such as proteins, membrane lipids such as sphingolipids, phospholipids or the like, or nucleic acids, etc. Preferably, the composition comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47% or 48% of impurities, the percentage being expressed by total weight of the composition.

Advantageously, the proportion of debris has the following composition:
from 35% to 45% of proteins,
from 2% to 10% of DNA,
from 10% to 20% of RNA,
from 10% to 15% of peptidoglycans,
from 2% to 5% of hydrocarbons,
from 5% to 10% of teichoic acid,
from 0.1% to 5% of soluble molecules, and
from 5% to 10% of ash,
the percentages being expressed by total weight of the cell debris composition.

It may also comprise soluble molecules such as antibiotics, siderophores and vitamins.

According to yet another advantageous aspect, the invention also relates to a microorganism extract comprising a lipid composition as described above.

Advantageously, the lipid composition represents at least 10% by weight of the total extract, preferably at least 40%. Even more advantageously, the lipid composition represents 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% by weight of the total extract.

The abovementioned microorganism extract also comprises cell debris specific for the microorganism in question. The major constituents (main atoms) of the cell biomass of several bacteria are given by way of example in table 1 below:

TABLE 1

| Major constituents of the cell biomass | |
|---|---|
| Microorganisms | Biomass composition |
| *Escherichia coli* | C H 1.77 O 0.49 N 0.24 |
| *Klebsiella aerogenes* | C H 1.75 O 0.43 N 0.22 |
| *Paraccocus denitrificans* | C H 1.81 O 0.51 N 0.20 |
| *Pseudomonas* C12B | C H 2.00 O 0.52 N 0.23 |
| *Aerobacter aerogenes* | C H 1.83 O 0.55 N 0.25 |
| *Streptomyces cattleya* | C H 1.60 O 0.58 N 0.17 |
| *Streptomyces clavuligerus* | C H 1.82 O 0.62 N 0.21 |
| *Corynebacterium glutamicum* | C H 1.77 O 0.49 N 0.22 |
| *Brevibacterium* ssp | C H 1.62 O 0.50 N 0.12 |
| Average | C H 1.80 O 0.50 N 0.20 |

These results have been obtained by analysis with a Thermo Fisher Flash 2000 series CHNS/O apparatus, sold by Thermo Scientific.

Preferably, the microorganism extract according to the invention comprises the conventional cell constituents: proteins, deoxyribonucleic acid (DNA), ribonucleic acid (RNA), phospholipids, triacylglycerols, soluble molecules, peptidoglycans, teichoic acid, carbohydrates and cellular ash.

According to one aspect of the invention, the present invention also relates to the use of a lipid composition as described above or of an extract as described above, for preparing biofuel, lubricant, surfactants, coatings (paints, inks, etc.), solvents or food ingredients or as synthesis intermediates for oleochemistry.

It is possible to obtain biodiesel by means of known processes, for example a process for transesterification of the triglycerides present in the composition according to the invention or the microorganism extract according to the invention, for the production of methyl esters of oils which serve as fuels under the name biodiesel.

Transesterification is a reaction comprising three reversible steps in series in which the triglycerides are converted to diglycerides, then the latter are converted to monoglycerides and, finally, the monoglycerides are converted to esters (biodiesel) and glycerol (co-product).

During the transesterification reaction, the oils or fats react with a short-chain alcohol (generally methanol) in the presence of a catalyst.

This reaction can be carried out by homogeneous catalysis, with catalysts that are soluble in the reaction medium, or by heterogeneous catalysis, with catalysts that are totally insoluble in the reagent.

At the current time, homogeneous catalysis is the technique most generally used in biodiesel production processes.

The transesterification can be carried out by basic or acid catalysis. A greater reactivity is generally obtained in a basic medium.

Three major classes of catalysts exist: basic catalysts, acid catalysts and the other catalysts.

By way of example, mention may be made of hydroxides, alkoxides or soaps of alkali metals or alkaline-earth metals (Li, Na, K, Ca, Ba, Cs, etc.), amines of the guanidine family; inorganic acids (HCl, $H_2SO_4$), sulfonic acids, ion exchange resins (strong acid), zeolites, titanium alkoxides (Ti(OBu)$_4$, Ti(OiPr)$_4$), and oxides of various metals (Sn, Mg, Zn, Ti, Pb).

The biodiesel obtained can be used as a mixture with diesel of fossil origin or pure, as a fuel.

The lubricant obtained from the composition according to the invention may also comprise additives that are generally used in a lubricant composition.

The invention also relates to a pharmaceutical or cosmetic composition comprising a lipid composition as described above, or an extract as defined above, in combination with a pharmaceutically or cosmetically acceptable carrier.

The abovementioned carboxylic acids, or fatty acids, of the composition, and in particular the fatty acids of anteiso form, are capable of advantageously protecting keratin-containing fibers against heat. The composition is therefore suitable for use in the temporary hot styling of hair, in particular human hair.

The invention advantageously relates to a cosmetic composition comprising a composition as defined above, in combination with a firming active substance, said cosmetic composition being in particular in the form of a foam.

Such a cosmetic composition can be used for styling keratin fibers. Thus, the invention advantageously relates to the use of the above-mentioned cosmetic composition for styling keratin fibers.

The composition according to the invention can be converted into quaternary ammonium and can thus be used (in an amount of 10%) in cosmetic products comprising at least one firming active substance and which are in particular in the form of a foam. It is thus possible to obtain a very long-lasting styling result, in particular with significant humidity in the air.

Quaternary ammonium or quaternary amine salts are produced by a quaternization reaction. It is generally a reaction between an alkylamine (or alkylamidoamine) and an alkyl halide or alkyl salt. For example, the reaction is carried out in two steps, a first step during which the fatty acids of the composition are reacted with an excess of dimethylaminopropylamine so as to form an alkylamidoamine, and a second step during which the alkylamidoamine of the first step reacts in turn with diethyl sulfate in the presence of butylene glycol so as to form the final quaternary ammonium that will be used in the cosmetic formulation of interest.

A firming active substance is known to those skilled in the art and can in particular be a vegetable or animal wax, for example beeswax.

The composition advantageously comprises ester derivatives chosen from the group made up of sterol esters, sugar esters, 2-ethylhexanol esters and higher alcohol esters, alone or as a mixture thereof.

These derivatives can be part of the formulation of cosmetic products or of medicaments for external use, in particular for topical applications to the skin.

The combination of the composition according to the invention with a pharmaceutically acceptable carrier makes it possible, for example, to optimize the moisturization of the skin, the straightening of the hair or an elastic effect on tissues. It may, moreover, have other effects, for instance the facilitated assimilation of a medicament.

For example, it is possible to encapsulate active ingredients in lipid vesicles having a composition such that they easily fuse with lipid membranes, thereby greatly facilitating the entry of the active ingredient into the cells. Advantageously, the lipid composition or the microorganism extract can be used as a medicament or a functional food (food supplement).

It can have an application in particular in the treatment of skin problems or also as a healing agent.

The invention will be understood more clearly on reading the figures and the examples which are given only by way of illustration and which are in no way limiting in nature.

BRIEF DESCRIPTION OF THE DRAWINGS

The various fatty acids present are given along the x-axis and the amount in µg/mg of dry biomass is expressed along the y-axis.

EXAMPLE 1: SYNTHESIS OF A LIPID COMPOSITION ACCORDING TO THE INVENTION BY MEANS OF A PROCESS FOR CULTURING A STRAIN OF *STREPTOMYCES*

Some species of *streptomyces*, like many other microorganisms, have the natural capacity to accumulate, in their cytoplasm, more than 40% of their dry weight in TAGs.

*Streptomyces*, like many other microorganisms, have the capacity to accumulate, in their cytoplasm, on average 20% of their weight in TAGs.

TAGs consist of one glycerol molecule and of three fatty acids (identical or different in nature) esterified on the hydroxyl groups of the glycerol.

In this example, the production of the lipid composition according to the invention was carried out using a culture of *streptomyces*, but could just have easily have been carried out using other bacterial strains of various genera of the actinomycete order, such as *Rhodococcus, Micrococcus* or *Actinomyces*.

A. Various Culture Processes

Several strains of *Streptomyces* are cultured according to various processes detailed below; culture with glucose as main carbon source (a), culture with glycerol as main carbon source (b), and culture with glycerol combined with phosphate hypercompensation (c).

The term "main carbon source" is intended to mean an amount of carbon-based compound which can be metabolized by the bacteria and which makes it possible to produce energy. The major carbon source represents more than 90% of the carbon supply in the culture or preculture medium.

(a) Culture of *Streptomyces lividans* TK24 and *Streptomyces coelicolor* M1146 in Glucose-Enriched Medium Spores ($10^6$) of two strains of *Streptomyces lividans* TK24 and *Streptomyces coelicolor* M1146 were plated out on an R2YE agar medium (55 mM glucose, 1 mM Pi) on the surface of which a cellophane porous to the nutritive elements of the medium was deposited. These strains were grown for 72 h at 28° C.

The R2YE medium has the following composition:
$K_2SO_4$ ($1.4 \cdot 10^{-3}$ mold and 0.25 g/l) MM=174 g/mol
$MgCl_2 \cdot 6H_2O$ ($5 \cdot 10^{-2}$ mold and 10.12 g/l) MM=203 g/mol.
Glucose or glycerol
Casein amino acids (0.1 g/l)
Supplementation after autoclaving as solid
$CaCl_2 \cdot 2H_2O$ ($2 \cdot 10^{-2}$ mold and 2.94 g/l) MM=147 g/mol
L-proline ($2.6 \cdot 10^{-2}$ mold and 3 g/l) MM=115 g/mol
TES buffer ($2.5 \cdot 10^{-2}$ mold and 5.73 g/l) MM=2304 g/mol
Trace elements (2 ml/l)
Yeast extract (5 g/l)
NaOH ($5 \cdot 10^{-3}$ mold and 0.2 g/l) MM=30 g/mol.

The composition obtained is analyzed following an extraction step and according to the analysis methods described in point B. The results are presented in FIG. 1 for the culture of *Streptomyces lividans* TK24 and in FIG. 2 for the culture of *Streptomyces coelicolor* M1146.

Figure 1:
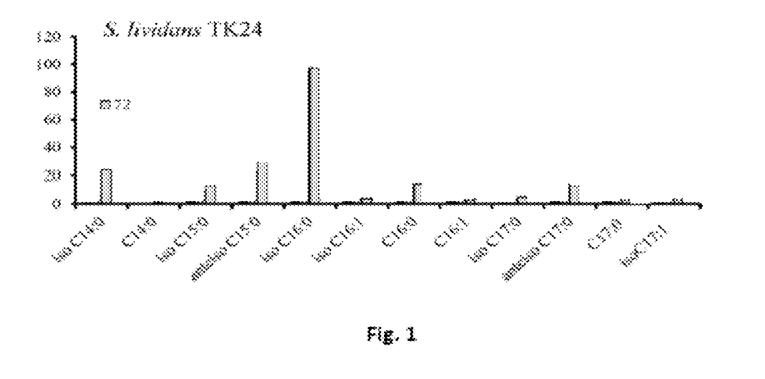
FIG. 1 represents the lipid profile of lipid compositions obtained by culturing the *Streptomyces lividans* TK24 strain in medium comprising glucose as main carbon source (55 mM) for 72 hours or 96 hours. The various fatty acids are given along the x-axis and the amount in µg/mg of dry biomass is expressed along the y-axis.

In FIG. 1, a composition having a large amount of iso C16:0 and anteiso C15:0 fatty acid is observed. These proportions are those of the invention, i.e. at least 50% of iso C16:0 and at least 8% of anteiso C15:0.

Figure 2:
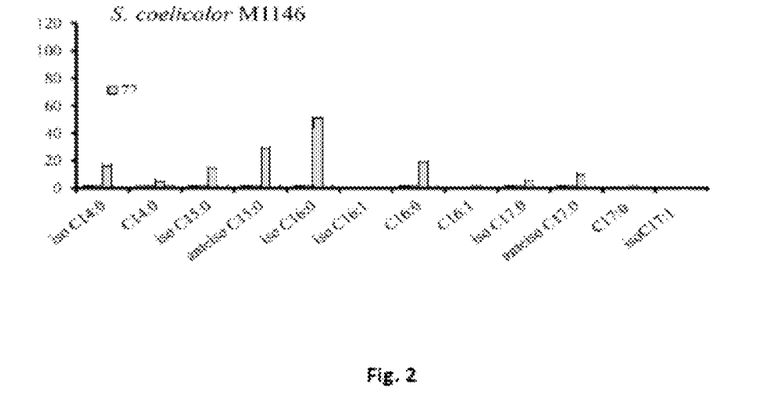
FIG. 2 represents the lipid profile of lipid compositions obtained by culturing the *Streptomyces coelicolor* M1146 strain in medium comprising glucose as main carbon source (55 mM) for 72 hours or 96 hours. The various fatty acids are given along the x-axis and the amount in µg/mg of dry biomass is expressed along the y-axis.

In an identical manner, in FIG. 2, a composition having a large amount of iso C16:0 and anteiso C15:0 fatty acid is observed, the proportions also being those of the invention, i.e. at least 50% of iso C16:0 and at least 8% of anteiso C15:0.

(b) Culture of *Streptomyces lividans* TK24 in Glycerol-Enriched Medium

Spores ($10^6$) of two strains of *Streptomyces lividans* TK24 were plated out on an R2YE agar medium containing purified or crude glycerol (Glycerine, Prolea) at various concentrations, on the surface of which a cellophane porous to the nutritive elements of the medium was deposited. These strains were grown for 96 h at 28° C.

The composition obtained is analyzed following an extraction step and according to the analysis methods described in point B. The results are presented in FIG. 3 for the culture on purified glycerol and in FIG. 4 for the culture in unrefined glycerol.

The crude glycerol can be purified by treatment with active carbon to remove the organic impurities, by alkaline treatment to remove the glycerol esters which have not reacted, and by ion exchange to remove the salts. The glycerol obtained by means of a series of distillations has a high purity (>99.5%), it is then said to be refined.

Figure 3:
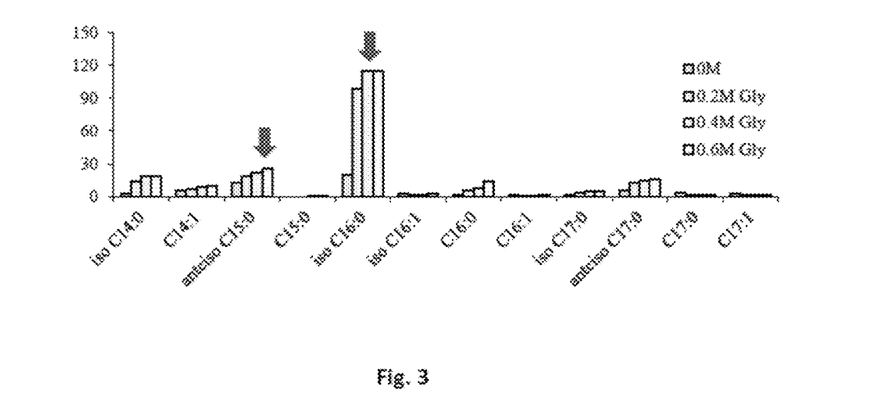
FIG. 3 represents the lipid profile of lipid compositions obtained by culturing the *Streptomyces lividans* TK24 strain in the presence of purified glycerol as main carbon source, for 96 hours, at various concentrations. The various fatty acids present are given along the x-axis and the amount in µg/mg of dry biomass is expressed along the y-axis.

It is observed in FIG. 3 that, in the presence of an amount of refined glycerol of greater than 0.2 M, the composition comprises an amount of iso C16:0 fatty acid of approximately 100 μm/mg of the dry weight, and approximately 30 μm/mg of the dry weight of anteiso C15:0 fatty acid.

Figure 4:
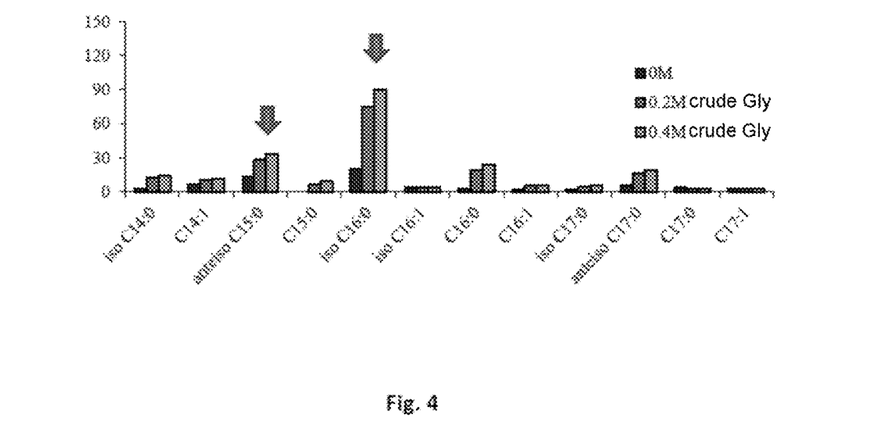
FIG. 4 represents the lipid profile of lipid compositions obtained by culturing the *Streptomyces lividans* TK24 strain in the presence of unrefined glycerol, i.e. crude glycerol, as main carbon source, for 96 hours, at various concentrations.
Figure 5:
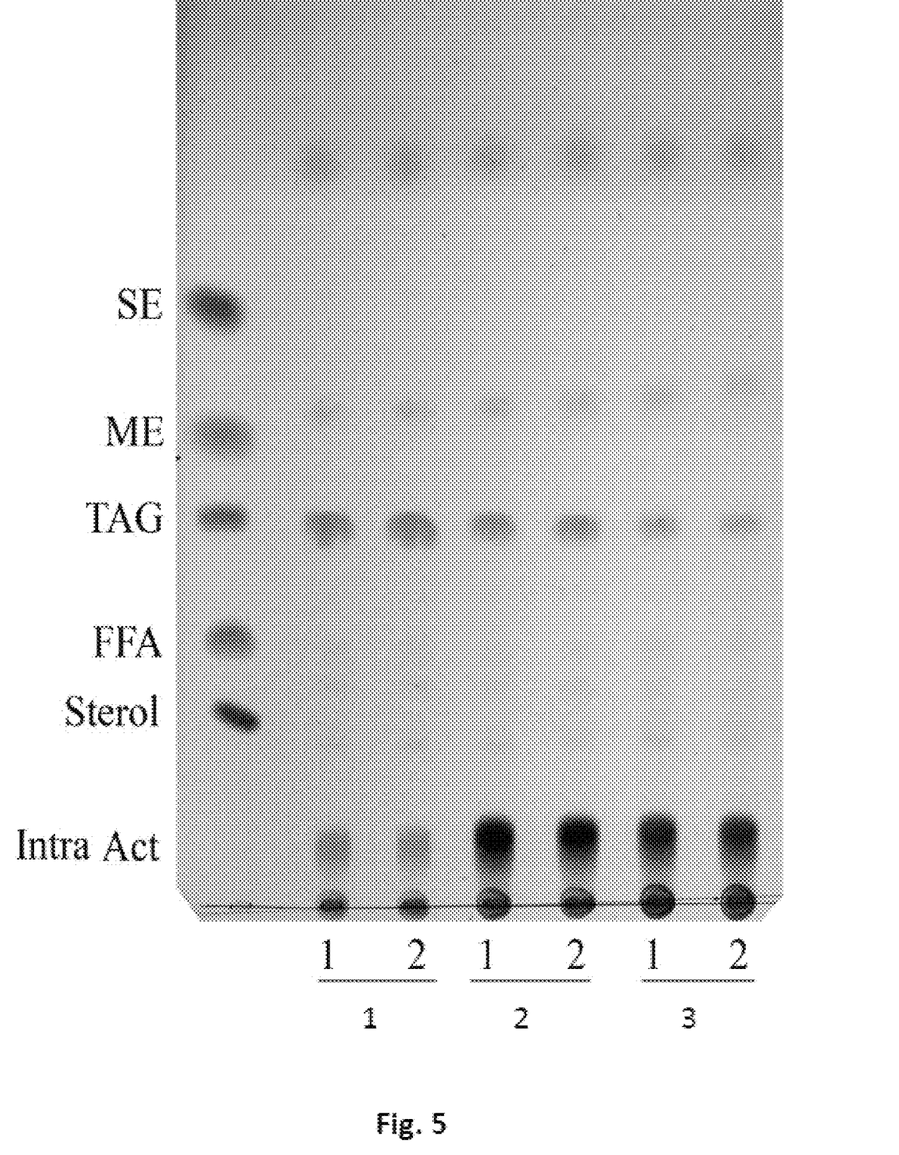
FIG. 5 represents a thin layer chromatography of lipid compositions according to the invention. These compositions are obtained using two cultures of three different strains of *streptomyces* (1: wild-type *Streptomyces lidivans* TK24; 2: *Streptomyces lidivans* TK24 mutant for the ppk gene; 3: *Streptomyces coelicolor* M145).

In an equivalent manner, it is observed in FIG. 4 that, in the presence of an amount of unrefined glycerol of greater than 0.2 M, the composition comprises an amount of iso C16:0 fatty acid of approximately 80 μm/mg of the dry weight, and approximately 30 μm/mg of the dry weight of anteiso C15:0 fatty acid.

(c) Culture of *Streptomyces coelicolor* M145 in Glycerol-Enriched Medium Combined with Phosphate Hypercompensation (P)

A strain of *Streptomyces lividans* TK24 was cultured for 96 h in R2YE liquid medium containing glycerol (0.2 M) and phosphate (1 mM).

The fatty acid composition obtained, following the extraction and analysis steps described in point B., is presented in table 2 below:

TABLE 2

Composition of the fatty acids present in the composition

| Fatty acids | Amount (g)[1] |
|---|---|
| iso C14:0 | 3.5 |
| C14:1 | 1.75 |
| anteiso C15:0 | 5 |
| C15:0 | 0.1 |
| iso C16:0 | 30 |
| iso C16:1 | 0.5 |
| C16:0 | 1.75 |
| C16:1 | 0.25 |
| iso C17:0 | 0.8 |
| anteiso C17:0 | 3.5 |
| C17:0 | 0.5 |
| C17:1 | 0.5 |

[1]values expressed per 100 g of the weight of the dry biomass.

It is observed that the composition comprises an amount of iso C16:0 fatty acid of approximately 30 g of the dry weight, and approximately 5 g of the dry weight of anteiso C15:0 fatty acid. These proportions are those of the invention, i.e. at least 50% of iso C16:0 and at least 8% of anteiso C15:0.

The lipid composition comprises short-chain fatty acids (from C14 to C17) which are mostly saturated. The composition also comprises methylated fatty acids (iso, anteiso) at more than 40 g of the weight of the dry biomass.

Similar results would have been obtained if the *Streptomyces* culture had been carried out with an excess and then a limitation of nitrogen (N) instead of phosphate, for the hypercompensation step.

B. Step of Extraction of the Fatty Composition from Cells and Determination of the Fatty Acid Nature of the Composition (Nature and Amount of Each FA):

The cell lysis can be carried out by any technique known from the prior art: through the action of a physical, chemical and/or biological agent. In the invention, the lysis of *Streptomyces* and the lipid extraction were carried out according to the method described in: "Folch, J., Lees, M. & Sloane Stanley, G. H. A simple method for the isolation and purification of total lipids from animal tissues. *J. Biol. Chem.* 226, 497-509 (1957)".

Thus, the lipids present in the composition are characterized and quantified.

A 2:1 chloroform/methanol mixture and silica plates of the type "silica G60, of dimension 20/20 cm and thickness 0.25 mm", sold by Merck (Germany) are used.

The lipid separation is carried out using a two-solvent system.

Solvent A (half-plate migration) is made up of petroleum ethyl ether/ether/acetic acid in proportions such as 20/20/0.8 (vol/vol/vol).

Solvent B (complete migration) is made up of petroleum diethyl ether/ether in proportions such as 49/1 (vol/vol).

At the end of the migration, the visualization is carried out with $MnCl_2$ using the carbonization method: the silica plate is incubated for one minute in a solution containing 120 ml of methanol, 120 ml of water, 0.8 g of $MnCl_2$ and 8 ml of sulfuric acid and is then heated in an oven at 100° C. until the dark lipid spots appear.

The lipid identification is determined using lipid migration standards (Sigma-Aldrich).

The coloration of the lipids was then recorded using the LAS-3000 imaging system and the Multigauge software from Fujifilm.

The results obtained are presented in figure X which represents a thin layer chromatography. It is noted that the composition comprises more than 50% of TAG.

The fatty acid composition can also be analyzed by gas chromatography (GC), after a step of conversion into methyl esters which is required for the analysis known to those skilled in the art, according to the Browse et al. (1986) procedure.

The GC analysis of fatty acid methyl esters is carried out with a 7890A chromatograph (Agilent) with a 30 m×0.25 mm factor four VF-23 ms capillary column.

The vector gas is helium having an input pressure of 1 ml/min.

The column temperature program is as defined hereinafter:
begin at 40° C. for 1 minute,
raise the column temperature to 130° C. by increases of 40° C. per minute,
maintain for 1 minute at a temperature of 130° C.,
raise the column temperature to 160° C. by increases of 1° C. per minute,
maintain for 1 minute at 160° C.,
raise the column temperature to 210° C. by increases of 40° C. per minute, and
maintain for 4 minutes at 210° C.

Once the passing through the column is complete, the identification of the peaks obtained is based on comparisons with standardized retention times (Sigma-Aldrich).

The quantification is carried out by flame ionization detection at 270° C.

The total amount of fatty acids is calculated from the ratio of the sum of the areas of the FAME peaks to the area of the octadecanoic acid methyl ester peak (Sigma-Aldrich).

EXAMPLE 2: COMPOSITION OF AN EXTRACT OF *S. COELICOLOR* M145 COMPRISING THE COMPOSITION ACCORDING TO THE INVENTION

The composition of the extract of *S. coelicolor* M145 obtained in point (c) is analyzed hereinafter.

The amino acid, fatty acid, nucleic acid and sugar composition of *S. coelicolor* is based on the one published by Borodina (Borodina et al., 2005b).

Atoms present in the extract of *Streptomyces coelicolor*: C H 1.62 O 0.45 N 0.25

Nature of the constituents:

TABLE 3

Composition of the *S. coelicolor* M145 biomass
(μmol (gram of dehydrated cells)$^{-1}$)

| Macromolecules | Data from the literature (% CDW) | Weight calculated from the theoretical composition (% CDW) | RSD (%) |
|---|---|---|---|
| Proteins | 41.2 | 41.1 | 0.17 |
| DNA | 3.6 | 6.0 | 35.36 |
| RNA | 16.7 | 16.7 | 0.00 |
| Phospholipids | 2.7 | 3.3 | 14.14 |
| Triacylglycerols | 1.8 | 2.0 | 7.44 |
| Soluble molecules | 3.0 | 2.6 | 10.10 |
| Peptidoglycan | 11.0 | 11.4 | 2.53 |
| Carbohydrates | 4.4 | 4.4 | 0.00 |
| Teichoic acid | 6.6 | 6.8 | 2.11 |
| Ash | 9.0 | 5.7 | 31.75 |
| Total | 100.0 | 100.0 | 0.00 |

The values of the main polymers which are part of the composition of the *S. coelicolor* biomass, namely the proteins, represent 41.2% and the nucleic acids 20.3% of the dry weight.

Contrary to the *coelicolor* M145 strain, the *S. coelicolor* M1146 strain (strain deleted for the main antibiotic biosynthesis pathways) has a TAG content which reaches 30% with respect to glucose and 40% with respect to glycerol.

EXAMPLE 3: COMPOSITION ACCORDING TO THE INVENTION USED AS BASIC OIL IN A LUBRICANT

The composition according to the invention can be transesterified by TMP (trimethylolpropane) and used as basic oil in a lubricant.

In this use, the portion of saturated compounds is predominant compared with that of the unsaturated compounds. In relative proportion, the percentage of unsaturated compounds is about 1% to 12% relative to the weight of the composition.

Such a composition has the advantage of being more stable with respect to cold and to oxidation than a derivative containing mainly unsaturated fatty acids. Moreover, said composition has the advantage of being more accessible in terms of cost and of availability compared with the isostearic acid derivatives currently used.

The cold-stability and oxidation-stability properties generally measured for a lubricating composition based on a basic oil of TMP derivative type are obtained, as indicated hereinafter:

| Properties | Standard | Unit | TMPTO (unsaturated fatty acid base) = reference | TMPTI (saturated branched acid base) |
|---|---|---|---|---|
| Viscosity (40° C.) | ASTM D445 | mm$^2$/s | 46 | 68 |
| Pour point | ASTM D97 | ° C. | −50 | −40 |

-continued

| Properties | Standard | Unit | TMPTO (unsaturated fatty acid base) = reference | TMPTI (saturated branched acid base) |
|---|---|---|---|---|
| RPVOT* | ASTM D2272 | Minutes | 180 | 800 |

*RPVOT, or rotating pressure vessel oxidation test, is carried out on the composition, plus 1.5% of Additin RC 9321 (RheinChemie).

The use of oil comprising the composition according to the invention thus provides a good compromise between cold-stability and oxidation-stability.

For example, 5% to 95% of oil with said composition incorporated into a basic oil for a lubricant makes it possible to provide these properties.

The invention claimed is:

1. A composition comprising: transesterified fatty acids derived from transesterifying triacylglycerols of a lipid, in which:
    at least 50% of fatty acids of the triacylglycerols are 14-methylpentadecanoic acids, and
    at least 8% of fatty acids of the triacylglycerols are 12-methyltetradecanoic acids, the percentages being expressed by weight of total fatty acids of the lipid.

2. The composition according to claim 1, wherein at least 55% by weight of the total fatty acids of the lipid are 14-methylpentadecanoic acids.

3. The composition according to claim 1, further comprising from 6.5% to 20% of 12-methyltridecanoic fatty acid, the percentage being expressed by weight of the total fatty acids of the lipid.

4. The composition according to claim 1, further comprising from 6.5% to 20% of 14-methylhexadecanoic fatty acid, the percentage being expressed by weight of the total fatty acids of the lipid.

5. The composition according to claim 1, wherein the lipid further comprises one or more fatty acids of the triacylglycerols chosen from the group consisting of 12-methyltridecanoic acid (iso C14:0/iso-tetradecanoic acid), tetradecenoic acid (C14:1), 12-methyltetradecanoic acid (anteiso C15:0/anteiso-pentadecanoic acid), pentadecanoic acid (C15:0), 14-methylpentadecanoic acid (iso C16:0/iso-hexadecanoic acid), 14-methylpentadecenoic acid (iso C16:1/iso-hexadecenoic acid), hexadecanoic acid (C16:0), hexadecenoic acid (C16:1), 15-methylhexadecanoic acid (iso C17:0/iso-heptadecanoic acid), heptadecanoic acid (C17:0), heptadecenoic acid (C17:1) and 14-methylhexadecanoic acid (anteiso C17:0/anteiso-heptadecanoic acid).

6. The composition according to claim 1, wherein the total fatty acids of the lipid are present in proportions of:
    from 6.7% to 7.7% of iso C14:0,
    from 3.1% to 4% of C14:1,
    from 9.8% to 11% of anteiso C15:0,
    from 0.1% to 0.7% of C15:0,
    from 61.5% to 62.5% of iso C16:0,
    from 0.5% to 1.5% of iso C16:1,
    from 3.1% to 4% of C16:0,
    from 0.1% to 7.7% of C16:1,
    from 0.5% to 1.5% of C17:0,
    from 0.5% to 1.5% of C17:1,
    from 1.1% to 2.1% of iso C17:0,
    and
    from 6.7% to 7.7% of anteiso C17:0,
    the percentages being expressed by weight of the total fatty acids of the lipid.

7. The composition according to claim 1, further comprising any other type of lipids, the lipids being free fatty acids, oligomers, sterols, fatty acid esters, sterol esters, monoacylglycerols and/or diacylglycerols.

8. A pharmaceutical or cosmetic composition comprising the composition as claimed in claim 1, alone or in combination with a pharmaceutically or cosmetically acceptable carrier.

9. The cosmetic composition as claimed in claim 8, in combination with a firming active substance.

10. A method for styling keratin fibers comprising applying to keratin fibers the cosmetic composition as claimed in claim 8.

11. The cosmetic composition as claimed in claim 9, which is in the form of a foam.

12. The composition of claim 1, wherein the triacylglycerols are transesterified with a short-chain alcohol.

13. The composition of claim 12, wherein the short-chain alcohol is methanol.

14. The composition of claim 12, wherein the short-chain alcohol is trimethylolpropane (TMP).

15. The composition according to claim 1, wherein the lipid comprises up to 10% of impurities.

* * * * *